(12) United States Patent
Zagami et al.

(10) Patent No.: US 12,046,343 B1
(45) Date of Patent: Jul. 23, 2024

(54) SYSTEMS AND METHODS FOR AUTOMATICALLY IDENTIFYING GOOD FAITH DISPENSING RED FLAGS

(71) Applicant: WALGREEN CO., Deerfield, IL (US)

(72) Inventors: Patricia Zagami, Indian Rocks Beach, FL (US); Patricia Daugherty, Highland Park, IL (US); Jon J. Arends, Chicago, IL (US); Edward J. Bratton, Gurnee, IL (US)

(73) Assignee: WALGREEN CO., Deerfield, IL (US)

( * ) Notice: Subject to any disclaimer, the term of this patent is extended or adjusted under 35 U.S.C. 154(b) by 658 days.

(21) Appl. No.: 17/065,845

(22) Filed: Oct. 8, 2020

(51) Int. Cl.
*G16H 20/13* (2018.01)
*G06N 20/00* (2019.01)

(52) U.S. Cl.
CPC ............. *G16H 20/13* (2018.01); *G06N 20/00* (2019.01)

(58) Field of Classification Search
CPC ............................... G16H 20/13; G06N 20/00
See application file for complete search history.

(56) References Cited

U.S. PATENT DOCUMENTS

| | | | |
|---|---|---|---|
| 2016/0055315 A1* | 2/2016 | Abbott | G16H 20/10 705/2 |
| 2018/0121620 A1* | 5/2018 | Bastide | G06F 16/334 |
| 2020/0051679 A1* | 2/2020 | Bostic | G16H 10/60 |

FOREIGN PATENT DOCUMENTS

| | | | | |
|---|---|---|---|---|
| WO | WO-9622577 A1 * | 7/1996 | | G06F 19/00 |

OTHER PUBLICATIONS

The Washington State Legislature. The Washington State Legislature WAC 246-919-985: Prescription monitoring program-Required registration, queries, and documentation. (Year: 2019).*
Sharma, Brihat. Opioid misuse detection in hospitalized patients using convolutional neural networks. Loyola University Chicago. 2019. (Year: 2019).*
Gregory, Thomas. The Role of Pharmacists in Safe Opioid Dispensing. Journal of Pharmacy Practice. First published Jun. 30, 2019 , vol. 33(6) 856-862. (Year: 2019).*

(Continued)

*Primary Examiner* — Jason S Tiedeman
*Assistant Examiner* — Tristan Isaac Evans
(74) *Attorney, Agent, or Firm* — MARSHALL, GERSTEIN & BORUN LLP; Randall G. Rueth

(57) ABSTRACT

Systems and methods for identifying Good Faith Dispensing red flags, as well as evidence to support the validity of a prescriptions for any red flags, associated a patient's attempting to fill a prescription for a controlled substance based on input from pharmacists as well as patient information coordinated across a network of pharmacies are provided herein. An exemplary computer-implemented method may include receiving a request to dispense a medication prescribed to a patient, collecting information associated with the patient, and identifying, based on one or more of the medication and the information associated with the patient, one or more red flags associated with dispensing the medication to the patient. The method may further include determining, based on the one or more identified red flags associated with dispensing the medication to the patient, whether dispensing the medication to the patient would violate any regulations, and if so, preventing the dispensing of the medication to the patient.

19 Claims, 9 Drawing Sheets

(56) References Cited

OTHER PUBLICATIONS

Fundin, Jeffery. Don't Ignore These Opioid Abuse Red Flags. Pharmacy Times. Oct. 18, 2017 (Year: 2017).*
The Commonwealth of Pennsylvania & The Pennsylvania Pharmacists Association. Prescribing Guidelines for Pennsylvania: Opioid Dispensing Guidelines. Jan. 14, 2016. (Year: 2016).*
The Washington State Legislature. The Washington State Legislature WAC 246-919-985: Prescription monitoring program-Required registration, queries, and documentation. 2019. (Year: 2019).*
Strand (Moving opioid misuse prevention upstream: A pilot study of community pharmacists screening for opioid misuse risk. Research in Social and Administrative Pharmacy 15 (2019) 1032-1036. (Year: 2019).*

* cited by examiner

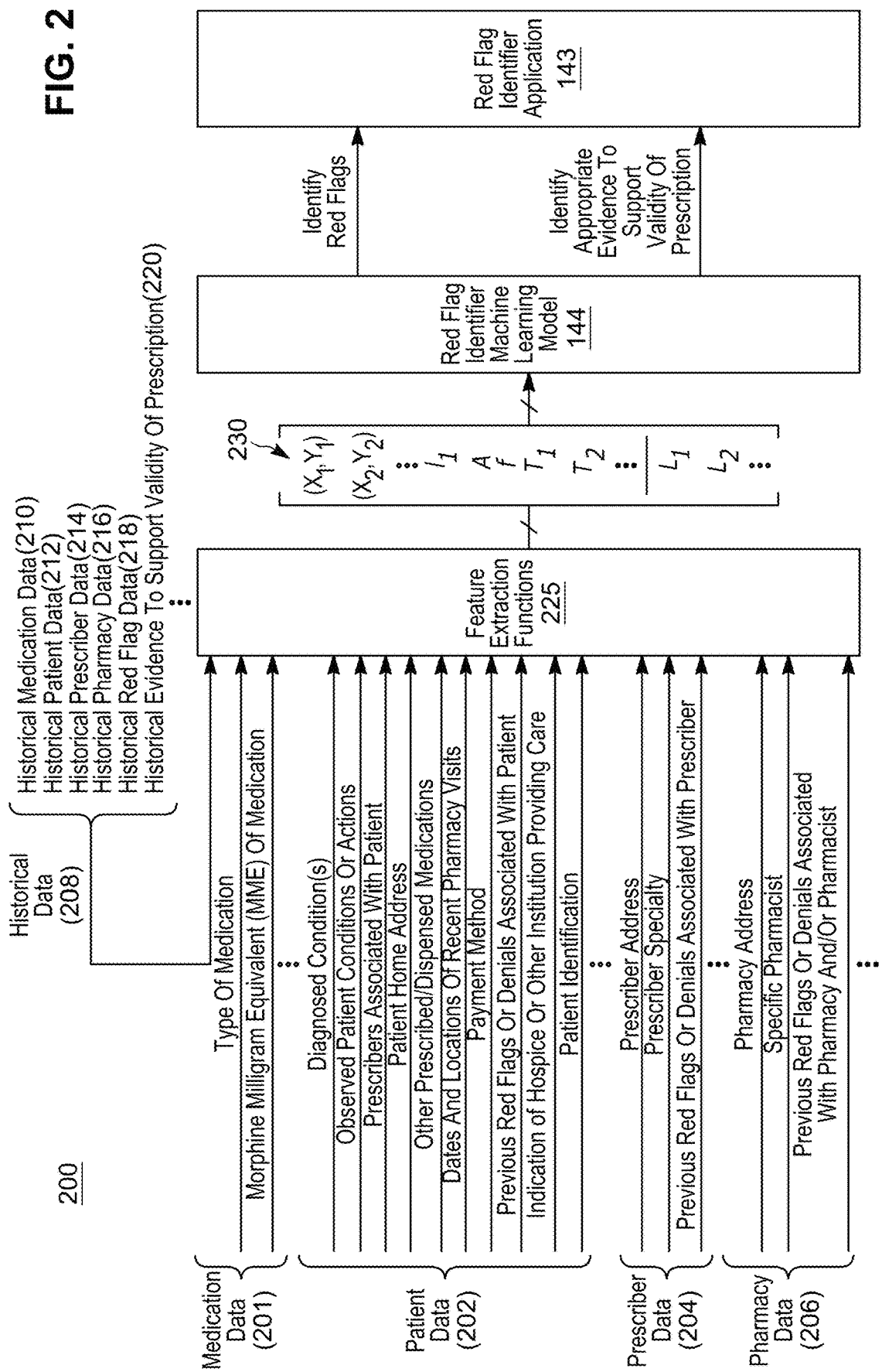

GFD Review Worksheet

Jon Testing | 12/10/1979 | 34 | M | (111) 222-3333 | 200 Wilmot Road, Chicago

Rx #: 663745 | 59393 | Select

Name: _Jon Testing_  Initials _A_  Date _4/28/14_  Promised Time ____
Address: _300 Wilmot Road_  AL/HC _NKDA_
Phone #: _(111) 333-2222_  Birth Date _12/10/1979_

_Lyrica 50 mg_
_QD_
_#30 TRF_

Dr. _Jonah Hill_
Refill ____  Address ____
Phone#: _(333) 222-1111_  DEA/NPI# _CC445110_
VM/Caller ID _MD_

Drug: LYRICA 50MG CAPSULES
Generic For: ____
Directions: TAKE ONE CAPSULE BY MOUTH EVERY DAY
Quantity: 30  Refills: 0
Qty Dispensed: 30  Refills Before: 10/09/2014

Name: JONAH | HILL
PBR DEA: CC445110  PBR NPI: 2526666666
Phone: (222) 333-4444  State: IL

Prescription MME: 50

California DRIVER LICENSE
_Jon Testing_

NarxCare

Narx Scores
Narcotic 845
Sedative 582
Stimulant 000

Overdose Risk Scores
710
(range 0-999)

[View PDMP]  [History...]

Clinical Justification
☒ Naloxone Rx
☒ Diagnosis: Cancer
☐ Hospice
☒ No Previous Denials
☒ Pbr Clarification ☒ 3rd Party Insurance
☒ ID on File

Notes:
_Spoke with prescriber - patient is far from home due to specialty referral for metastatic cancer progression. Patient history shows naloxone counseling and dispensing within past 3 month_

Red Flags
☒ Proximity/Location — _Medical referral to specialist_
☐ High Risk Combination
☒ Poly Pharmacy — _Medical referral to specialist_
☐ Outside of Pbr Scope
☒ NarxCare over 500 — _Increasing severity of cancer_
☐ Cash/Discount
☐ Poly-Prescriber
☐ Pat appears intoxicated

[Update Rx] [Create Exception] [Accept] [Reject] [Consult Req]

| Application | Patient | Utilities | Window | | | | |
|---|---|---|---|---|---|---|---|
| Jon Testing | | M | 12/10/1979 | 34 | 200 Wilmot Road, Chicago | (111) 222-3333 | |

Good Faith Dispensing Counseling Worksheet

☐ Patient ID Not on File; Scan ID before dispensing
☑ Offer Naloxone
☐ Opioid Naive - Safe Medication Use Counseling
☐ Opioid Assessment - Chronic Use

[Save]  [Cancel]

JON | NSJ | CENT | 7:43 AM

FIG. 3D

SYSTEMS AND METHODS FOR AUTOMATICALLY IDENTIFYING GOOD FAITH DISPENSING RED FLAGS

FIELD OF THE DISCLOSURE

The present disclosure generally relates to regulating controlled substances and, more particularly, to automatically identifying red flags associated with dispensing a controlled substance to a particular patient.

BACKGROUND

Generally speaking, pharmacists who dispense controlled substance prescriptions have a responsibility to ensure that the controlled substance prescription is dispensed for a legitimate medical purpose in the usual course of professional practice. Specifically, pharmacists have a corresponding responsibility to use their professional judgement to evaluate the validity of prescriptions in conjunction with state and federal controlled substance laws when dispensing all prescriptions.

Currently, pharmacists may utilize cognitive or a paper-based checklists when filling prescriptions for controlled substances in order to determine whether the controlled substance prescription is dispensed for a legitimate medical purpose. Generally speaking, the checklist requires the pharmacist to check for "red flags" associated with dispensing the controlled substance to a particular patient, i.e., indications of risks associated with dispensing the controlled substance to the patient. The pharmacist then determines whether there is evidence to support the validity of a prescriptions for any red flags associated with the patient as indicated by the checklist. For instance, the checklist may include a question regarding whether the patient has shown the pharmacist a valid ID, because a lack of valid ID is a red flag related to risks associated with dispensing controlled substances (e.g., because the patient may not be who they say they are). However, if the patient is known to pharmacy staff, and the pharmacy staff can identify him or her, this may be evidence to support the validity of a prescription for the patient not having his or her ID on hand. Based on completing the checklist and identifying possible evidence to support the validity of a prescriptions for any red flags, the pharmacist makes a determination as to whether the controlled substance prescription should be dispensed, and/or as whether a call to the prescriber is warranted prior to dispensing the controlled substance prescription.

However, there are several problems associated with using a paper checklist in this manner in order to determine whether to dispense a controlled substance prescription to a patient, especially in the context of a large nationwide network or chain of pharmacies. One problem associated with using a paper checklist in this manner is that there is no way of accounting for red flags that cannot be established based on a one-on-one interaction with a particular pharmacist. For instance, the paper checklist cannot easily coordinate information obtained by different pharmacies, e.g., in order to flag a patient who travels to multiple different pharmacies to access controlled substances. Another problem with using a paper checklist in this manner is that paper checklists are not easily updated, e.g., across a large nationwide network or chain of pharmacies, when new red flags associated with the abuse of controlled substances are discovered, or when new types or combinations of substances need to be controlled (e.g., based on new trends of drug abuse that arise over time).

SUMMARY

In an aspect, a computer-implemented method is provided, comprising: receiving, by one or more processors associated with a pharmacy, a request to dispense a medication prescribed to a patient; collecting, by the one or more processors, information associated with the patient; identifying, by the one or more processors, based on one or more of the medication and the information associated with the patient, one or more red flags associated with dispensing the medication to the patient; determining, by the one or more processors, based on the one or more identified red flags associated with dispensing the medication to the patient, that dispensing the medication to the patient would violate one or more regulations; and preventing, by the one or more processors, the medication from being dispensed to the patient based on determining that dispensing the medication to the patient would violate one or more regulations.

Moreover, in some examples, identifying the red flags may be further based on prescription information (e.g., including information about medication, dose, quantity, directions, refills, indications, etc.), prescriber information (e.g., including practice specialty, prescribing patterns and volumes, billing patterns, such whether the prescriber is a cash business, etc.), geographic, and combinations with other prescriptions for the same patient.

In another aspect, a computer system is provided, the computer system comprising: one or more processors; and a non-transitory program memory communicatively coupled to the one or more processors and storing executable instructions that, when executed by the one or more processors, cause the computer system to: receive a request to dispense a medication prescribed to a patient; collect information associated with the patient; identify, based on one or more of the medication and the information associated with the patient, one or more red flags associated with dispensing the medication to the patient; determine, based on the one or more identified red flags associated with dispensing the medication to the patient, that dispensing the medication to the patient would violate one or more regulations; and prevent the medication from being dispensed to the patient based on determining that dispensing the medication to the patient would violate one or more regulations.

In still another aspect, a tangible, non-transitory computer-readable medium storing executable instructions is provided that, when executed by at least one processor of a computer system, cause the computer system to: receive a request to dispense a medication prescribed to a patient; collect information associated with the patient; identify, based on one or more of the medication and the information associated with the patient, one or more red flags associated with dispensing the medication to the patient; determine, based on the one or more identified red flags associated with dispensing the medication to the patient, that dispensing the medication to the patient would violate one or more regulations; and prevent the medication from being dispensed to the patient based on determining that dispensing the medication to the patient would violate one or more regulations.

BRIEF DESCRIPTION OF THE DRAWINGS

FIG. 2 illustrates a block diagram of an example machine learning model which the system of FIGS. 1A-1C can use for identifying red flags associated with dispensing a controlled substance to a particular patient, in accordance with some embodiments.

FIGS. 3A-3D illustrate example user interface displays which may be used in the system of FIGS. 1A-1C for identifying red flags associated with dispensing a controlled substance to a particular patient, in accordance with some embodiments.

DETAILED DESCRIPTION

Figure 1A:
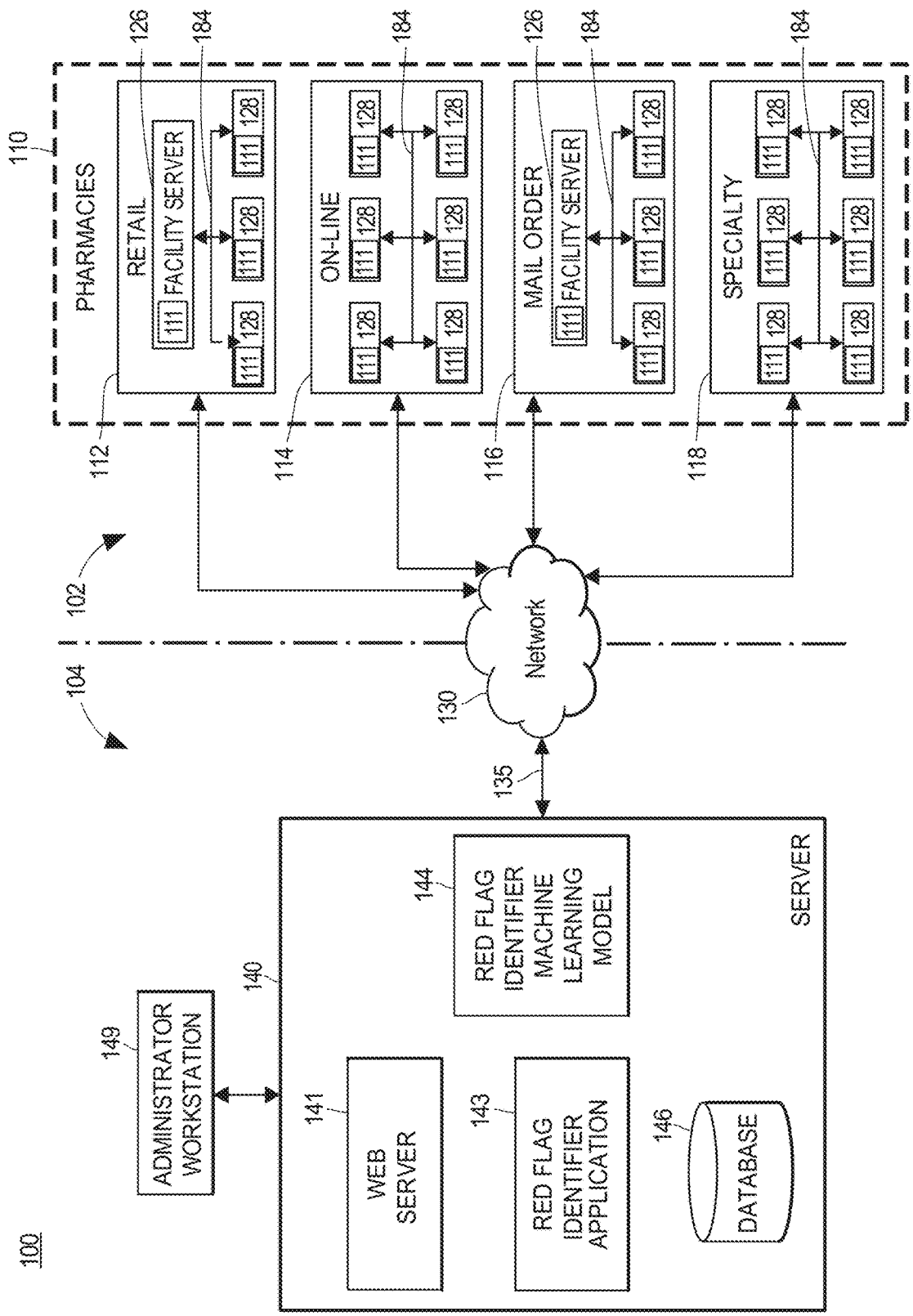
FIGS. 1A-1C illustrate block diagrams of a computer network, a computer server, and computing terminals on which an exemplary system for identifying red flags associated with dispensing a controlled substance to a particular patient may operate, in accordance with some embodiments.

The present application provides an automated system for identifying red flags, as well as evidence to support the validity of a prescription and any positive factors that support the validity of a prescription, associated with patients attempting to fill prescriptions for controlled substances based on input from pharmacists as well as information coordinated across a network of pharmacies. Advantageously, the automated system may allow pharmacists or other users to easily add new red flags and/or evidence to support the validity of a prescription for particular types of red flags, e.g., based on their observations or based on new emerging trends in the abuse of controlled substances, to the system implemented across the network of pharmacies. Moreover, in some examples, the automated system may utilize machine learning techniques to recognize red flags and/or appropriate evidence to support the validity of a prescription for red flags for particular patients based on historical data from the network of pharmacies. Additionally, the automated system may utilize machine learning techniques to identify new red flags and/or new evidence to support the validity of a prescription for particular types of red flags based on historical data from the network of pharmacies, and add new red flags and/or new evidence to support the validity of a prescription identified by the machine learning techniques to the system implemented across the network of pharmacies.

Based on identified red flags, evidence to support the validity of a prescription, and resolution for any red flags associated with dispensing a controlled substance to a particular patient, the system may identify next steps for a pharmacist to evaluate in order to prevent abuse of the controlled substance. For instance, in some examples, the system may determine whether or not the documented resolutions or evidence to support the validity of a prescription are sufficient for one or more of the identified red flags. Moreover, in some examples, based on the identified red flags and/or lack of appropriate evidence to support the validity of a prescription or documented resolution for any of the identified red flags, the system may determine that dispensing the controlled substance to the patient would violate one or more regulations associated with the controlled substance, and may notify the pharmacist that he or she should not dispense the controlled substance to the patient, or otherwise prevent the dispensing of the controlled substance to the patient until sufficient information has been documented. Furthermore, in some examples, the system may determine that the prescriber of the controlled substance should be contacted regarding the prescription of the controlled substance to the patient, and may notify the pharmacist that he or she should contact the prescriber, or may automatically initiate contact with the prescriber regarding the prescription of the controlled substance to the patient to obtain additional evidence that supports the validity of the prescription. Additionally, the system may update profiles to indicate red flags, evidence to support the validity of a prescription, and/or controlled substance denials associated with each patient and communicate these updates to other pharmacies in a network of pharmacies.

Figure 1B:
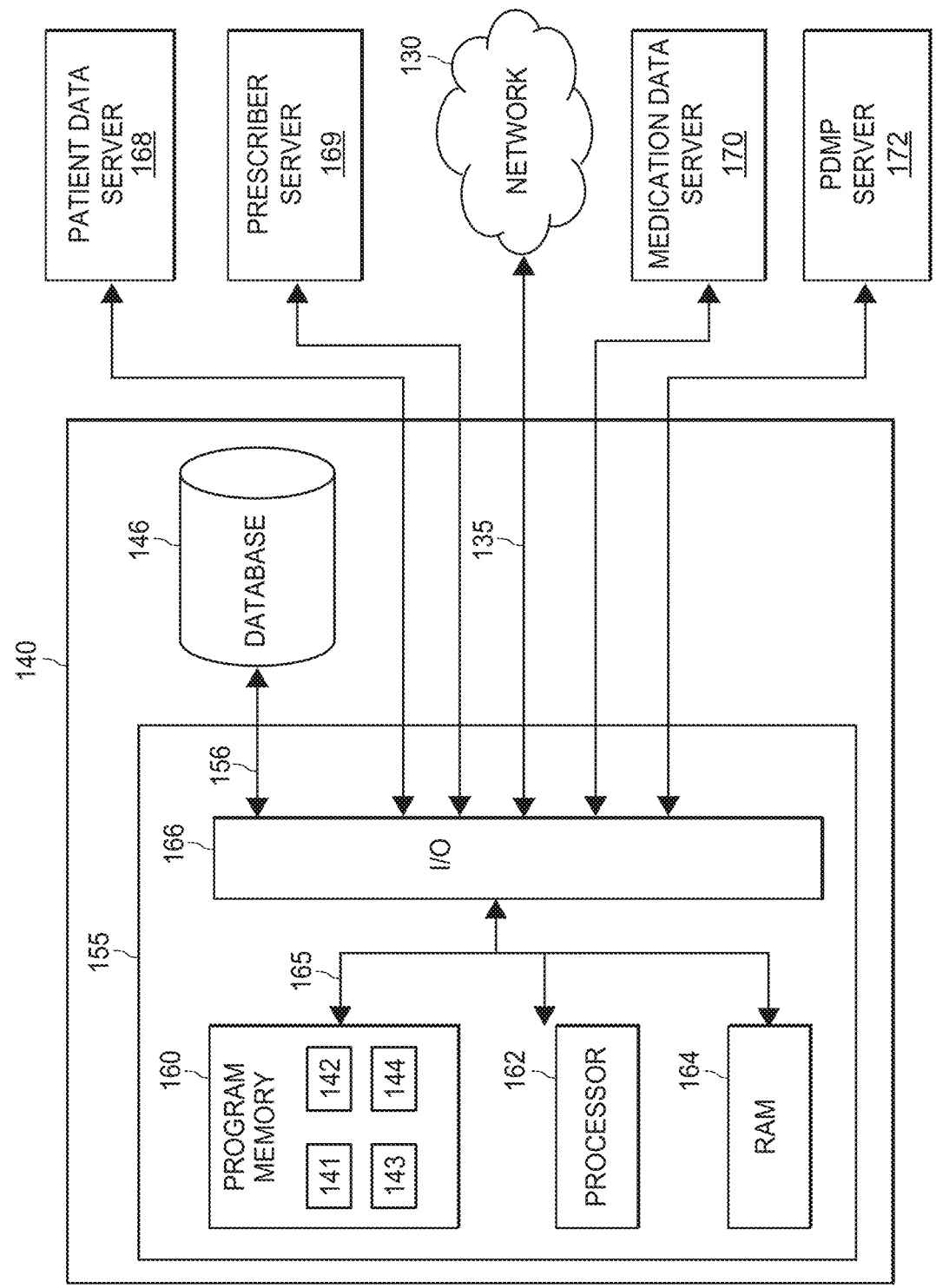
Figure 1C:
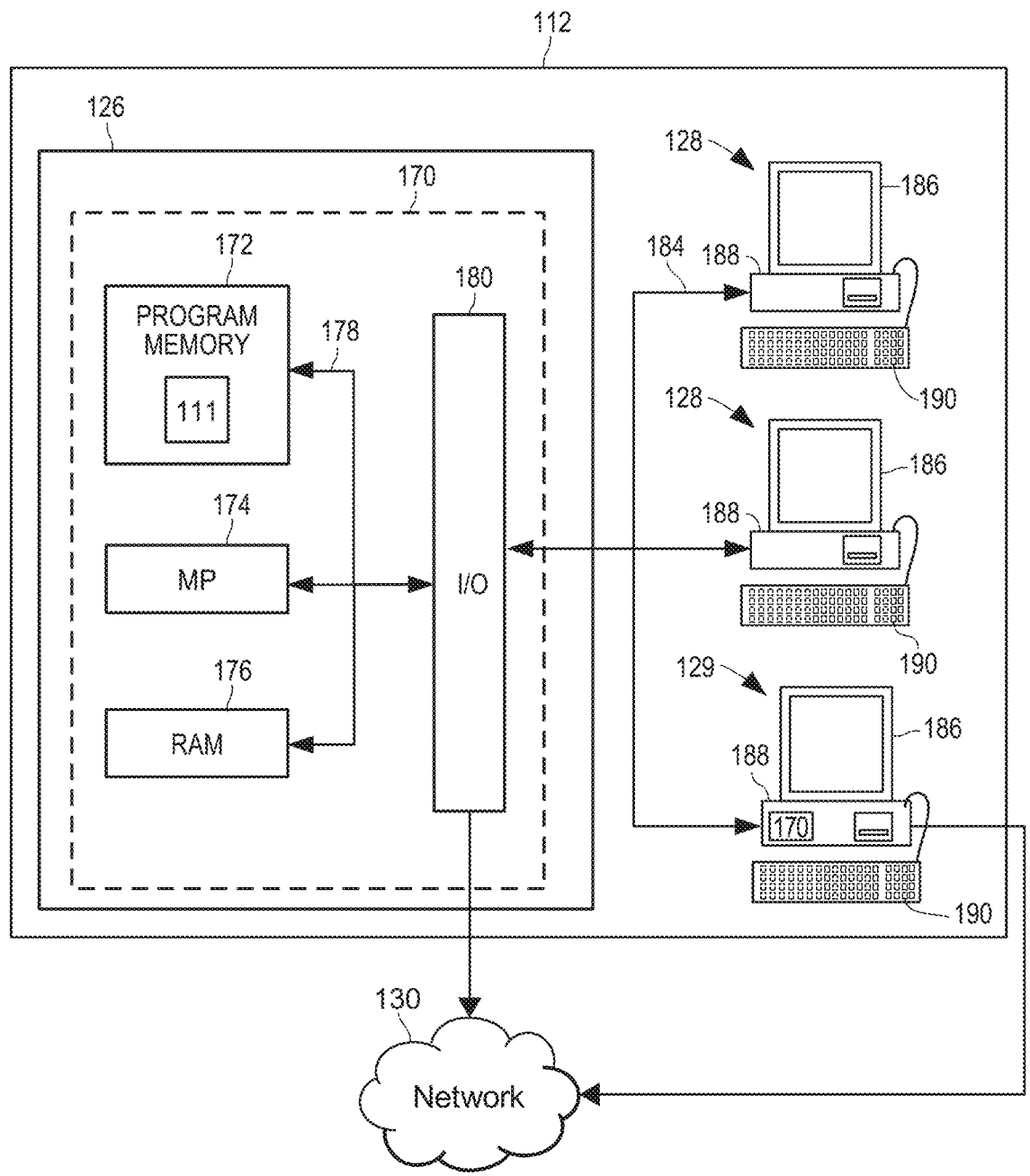

FIGS. 1A-1C illustrate block diagrams of a computer network, a computer server, and computing terminals on which an exemplary system 100 for identifying red flags associated with dispensing a controlled substance to a particular patient may operate, in accordance with some embodiments.

FIG. 1A illustrates a block diagram of an exemplary system 100 for identifying red flags associated with dispensing a controlled substance to a particular patient. The high-level architecture includes both hardware and software applications, as well as various data communications channels for communicating data between the various hardware and software components. The system 100 may be roughly divided into front-end components 102 and back-end components 104. The front-end components 102 may be disposed within one or more pharmacies 110. Where there is more than one pharmacy 110, the pharmacies 110 may be located, by way of example rather than limitation, in separate geographic locations from each other, including different areas of the same city or different states. The front-end components 102 may comprise a plurality of pharmacy workstations 128. The pharmacy workstations 128 may be local computers located in the various pharmacies 110 that execute a variety of applications related to pharmacy management. Pharmacists, technicians, or other users (not shown) may use the pharmacy workstations 128 to access patient information, enter new prescriptions, access insurance and payment information, and perform other pharmacy management-related tasks. Thus, the front-end components 102 may include pharmacy workstations 128 for servicing patients visiting an in-store retail pharmacy 112, pharmacy workstations 128 for servicing patients who choose to fill their prescriptions through an on-line pharmacy 114, a plurality of pharmacy workstations 128 for servicing patients who prefer to use the services of a mail-order pharmacy 116, and a plurality of pharmacy workstations 128 for servicing patients who require the services of a specialty pharmacy 118.

The front-end components 102 may also comprise a plurality of facility servers 126 disposed at the pharmacies 110, instead of or in addition to a plurality of pharmacy workstations 128. Each pharmacy 112, 114, 116, 118 may include one or more facility servers 126 that may be utilized to facilitate communications between the pharmacy workstations 128 and the back-end components 104 via a network 130, described below, and to store information for a plurality of patients, employees, accounts, or other records associated with each facility. Further, each pharmacy 112, 114, 116, 118 may include one or more pharmacy workstations 128 operatively connected to the facility server 126 via a local network 184.

The front-end components 102 may communicate with the back-end components 104 via the network 130. The network 130 may be a proprietary network, a secure public internet, a virtual private network or some other type of network, such as dedicated access lines, telephone lines, satellite links, cellular data networks, combinations of these, etc. Where the network 130 comprises the Internet, data communications may take place over the network 130 via an Internet communication protocol. The back-end components 104 include one or more servers 140. Each server 140 may include one or more computer processors adapted and configured to execute various software applications and components of the system 100, in addition to other software applications. The server 140 may further include a database 146 that is adapted to store, inter alia, patient information associated with both current and historical patients, as well as information associated with medications, pharmacies, and prescribers, in various embodiments. The server 140 may access data stored in the database 146, as well as data stored in other systems (not shown) when executing various functions and tasks associated with the operation of the system 100.

Although the system 100 is shown to include one server 140 and four pharmacies 112, 114, 116, and 118, it should be understood that different numbers of each may be utilized in various embodiments. For example, the system 100 may include a plurality of servers 140 and hundreds of pharmacies 110, all of which may be interconnected via the network 130. Furthermore, the database storage or processing performed by the one or more servers 140 may be distributed among a plurality of servers 140 in an arrangement known as "cloud computing." This configuration may provide various advantages, such as enabling near real-time uploads and downloads of information as well as periodic uploads and downloads of information. This may in turn support a thin-client embodiment of the pharmacy workstations 128, wherein most of the processing and storage is performed by the servers 140.

FIG. 1B is a schematic diagram of one possible embodiment of the server 140. The server 140 may have a controller 155 that is operatively connected to the database 146 via a link 156. It should be noted that, while not shown, additional databases may be linked to the controller 155 in a known manner. The controller 155 may include a program memory 160, a processor 162 (which may be called a microcontroller or a microprocessor), a random-access memory (RAM) 164, and an input/output (I/O) circuit 166, all of which may be interconnected via an address/data bus 165. It should be appreciated that although only one processor 162 is shown, the controller 155 may include multiple processors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM 164 and program memories 160 may be implemented as semiconductor memories, magnetically readable memories, or optically readable memories, for example. The controller 155 may also be operatively connected to the network 130 via a link 135. In some examples, the server 140 may communicate with one or more patient data servers 168, e.g., via the network 130. For example, the server 140 may request information associated with current and/or historical patients from the patient data server 168, and/or the patient data server 168 may automatically transmit this information to the server 140. Additionally, in some examples, the server 140 may communicate with one or more prescriber servers 169, e.g., via the network 130. For instance, the server 140 may request information related to which medications have been prescribed to a particular patient by various prescribers, as well as information about the prescribers themselves, from the prescriber data servers 169, and/or the prescriber data server 169 may automatically transmit this information to the server 140. For instance, one or more of the patient data server 168 and/or the prescriber data server 169 may be servers associated with doctors' offices or healthcare systems associated with current or historical patients. Furthermore, in some examples, the server 140 may communicate with one or more medication data servers 170, e.g., via the network 130. For instance, the server 140 may request information related to different types of medications from the medication data server 170, and/or the medication data server 170 may automatically transmit this information to the server 140. Additionally, in some examples, the server 140 may communicate with one or more prescription drug monitoring program (PDMP) servers 172 that store controlled substance data aggregated from multiple pharmacies by governmental organizations, i.e., for use in law enforcement. Although the patient data server 168, prescriber server 169, medication data server 170, and PDMP server 172 are illustrated as separate servers in FIG. 1B, in some examples, the functionalities described as being performed by each of these servers may be performed by one server, or by more than three servers.

FIG. 1C is a schematic diagram of one possible embodiment of the front-end components 102 located in one or more of the pharmacies 110 from FIG. 1A, such as pharmacy 112. Although the following description addresses the design of the pharmacies 110, it should be understood that the design of one or more of the pharmacies 110 may be different than the design of other pharmacies 110. Also, each of the pharmacies 110 may have various different structures and methods of operation. It should also be understood that the embodiment shown in FIG. 1C illustrates some of the components and data connections present in an exemplary pharmacy 112, however it does not illustrate all of the data connections present in a typical pharmacy. For exemplary purposes, one design of a pharmacy is described below, but it should be understood that numerous other designs may be utilized.

Each pharmacy 110 may have one or more pharmacy workstations 128 or one or more facility servers 126. The facility server 126 may be operatively connected to a plurality of pharmacy workstations 128 via a network 184. The network 184 may be a wide area network (WAN), a local area network (LAN), or any other type of network readily known to those persons skilled in the art. The facility server 126 or workstations 128 may also be operatively connected to the server 140 via the network 130.

Each workstation 128 or facility server 126 includes a controller 170. Similar to the controller 155 from FIG. 1B, the controller 170 may include a program memory 172, a microcontroller or a microprocessor (MP) 174, a random-access memory (RAM) 176, and an input/output (I/O) circuit 180, all of which may be interconnected via an address/data bus 178. As discussed with reference to the controller 155, it should be appreciated that although only one microprocessor 174 is shown, the controller 170 may include multiple microprocessors 174. Similarly, the memory of the controller 170 may include multiple RAMs 176 and multiple program memories 172. Although the I/O circuit 180 is shown as a single block, the I/O circuit 180 may include a number of different types of I/O circuits. The RAM 176 and programs memories 172 may also be implemented as semiconductor memories, magnetically readable memories, and/or optically readable memories, for example. In some embodiments, the RAM 176 and program memories 172 may be combined into one memory without materially altering the system 100 as described herein.

The workstations 128 may further include user interface displays 186 and keyboards 190, as well as a variety of other input/output devices (not shown) such as scanners, printers, touch screens, track pads, track balls, voice recognition systems, digital cameras, etc. Pharmacists, technicians, or other users may sign on to the pharmacy workstations 128 using any available technique, such as entering a user name and password. If users are required to sign on to the pharmacy workstations 128, this information may be passed via the network 184 to the facility server 126, so that the controller 170 will be able to identify which users are signed on to the system.

In some embodiments, the patient system 100 may utilize a web interface to enable communication between the pharmacies 110 and the server 140, in which case the server 140 may include a web server 141. The web server 141 may be a stand-alone server, or a software module implemented within the server 140. The various front-end components 102 may include a web browser client application 111 to communicate with the back-end components 104. A web server 141 may transmit web pages to the facility servers 126 and pharmacy workstations 128 in response to URL requests received by the web server 141 from the front-end components 102 over the network 130. The web pages sent to the front-end components 102 may include data in the database 146. It should be noted that, while the current embodiment describes a web server 141 and a web browser client 111, each implementing the hyper-text transfer protocol, the web server 141 could implement any known or later-developed protocol compatible with the web browser client application 111 running on the front-end components 102 and adapted to the purpose of receiving and providing the necessary patient information via the network 130.

The server 140 may further include a number of software applications stored in a program memory 160. The software applications may be executed on the same computer processor as the web server application 141, or on different processors. The various software applications may include a red flag identifier application 143. Generally speaking, the red flag identifier application 143 may be configured to execute the steps of the method 400 discussed in greater detail below with respect to FIG. 4. In particular, the red flag identifier application 143 may be configured to determine whether there are any red flags associated with dispensing a prescribed medication to a particular patient. For instance, red flags may be indicators of risks associated with dispensing the prescribed medication to the patient, e.g., because the prescribed medication is a controlled substance, in combination with other factors determined based on patient information, prescriber information, etc., from a network or chain of pharmacies. In some examples, the red flag identifier application 143 may be configured to identify whether there is evidence to support the validity of a prescription. In some examples, the red flag identifier application 143 may determine that the prescriber of the medication should be contacted to confirm, e.g., that the medication was prescribed to the correct patient, that the correct medication was prescribed, to confirm details related to the patient's diagnosis, etc., and may prompt a pharmacist to contact the prescriber, or may automatically initiate contact with the prescriber, for confirmation. In any case, the red flag identifier application 143 may determine whether or not the medication can be dispensed to the patient without violating any regulations (e.g., state or federal regulations), based on any remaining (i.e., not resolved) red flags associated with dispensing the medication to the patient. If the red flag identifier application 143 determines that the medication can be dispensed to the patient without violating any regulations, the red flag identifier application 143 may facilitate the dispensing of the medication to the patient. On the other hand, if the red flag identifier application 143 determines that the medication cannot be dispensed to the patient without violating any regulations, the red flag identifier application may prevent the dispensing of the medication to the patient.

In some examples, the red flag identifier application 143 may be configured to train a red flag identifier machine learning model 144 to identify red flags and/or evidence to support the validity of a prescription associated with dispensing a controlled substance to a particular patient, and/or to identify new red flags associated with dispensing medications to patients. In particular, now referring to FIG. 2, the red flag identifier application 143 may train and operate the red flag identifier machine learning model 144 in accordance with the scheme 200. The red flag identifier application 143 can receive various input signals, including medication data 201 for medications prescribed to a current patient, patient data 202 for a current patient, prescriber data 204 for each prescriber associated with the current patient, pharmacy data 206 for each pharmacy associated with the current patient, historical data 208 for a plurality of historical patients, e.g., including historical medication data 210 for medications prescribed to the historical patients, historical patient data 212, historical prescriber data 212 for prescribers of medication to the historical patients, historical red flag data 216 for prescriptions prescribed to the historical patients, historical evidence data 220 supporting the validity of historical prescriptions documented by pharmacists, that resolve historical red flags, etc.

For example, the medication data 201 and/or historical medication data 210 may include indications of types of medications associated with current and/or historical patients, respectively. This information may include the type of medication (e.g., the particular prescribed medication, a classification of medication, such as opioid, amphetamine, etc., whether the medication is a controlled substance, etc.), the morphine milligram equivalent (MME) of the medication, etc. Additionally, the medication data 201 may include an indication of conditions typically treated by the medication, as well as an indication of other medications with which the medication should not be combined.

Moreover, the patient data 202 and/or historical patient data 212 may include various information associated with the current and/or historical patients, respectively, that is relevant for determining whether a prescribed medication should be dispensed to the patient. For instance, as a few examples, the patient data 202 and/or historical patient data 212 may include identification associated with the patient, diagnosed conditions associated with the patient, conditions or actions of the patient that are observed by a pharmacist, prescribers associated with the patient, the home address of the patient, dates and locations of recent pharmacy visits, payment methods used by the patient, previous red flags or denials associated with the patient, indications of whether the patient is being treated by hospice or other institutionalized care, etc.

Furthermore, the prescriber data 204 and/or historical prescriber data 214 may include various information associated with any prescribers of medication to the current and/or historical patients, respectively. For instance, as a few examples, the prescriber data 204 and/or historical prescriber data 214 may include addresses associated with prescribers and specialties associated with prescribers, indications of previous red flags or denials associated with prescribers, etc.

Similarly, the pharmacy data 206 and/or the historical pharmacy data 216 may include various information associated with any pharmacies that have dispensed or have been requested to dispense medications to the current and/or historical patients, respectively. As a few examples, the pharmacy data 206 and/or the historical pharmacy data 216 may include addresses associated with pharmacies, specific pharmacists at pharmacies who have dispensed or have been requested to dispense medications to the patient, previous red flags and/or denials associated with each pharmacy or pharmacist, etc.

Additionally, the historical red flag data 218 may include indications of historical patients' requests for dispensing prescribed medications that have been associated with red flags and/or denials (and which have not), while the historical evidence data 220 (to support the validity of historical prescriptions and/or historical red flag resolutions) may include indications of historical evidence to support the validity of a prescription appropriate for resolving historical red flags. In some examples, the historical red flag data 218 and/or historical evidence data 220 supporting the validity of historical prescriptions or red flag resolutions may include data derived from previous pharmacists' use of paper checklists, as well as data derived from the use of the system described herein with respect to FIGS. 1A-1C.

Generally speaking, the feature extraction functions 225 can operate on at least some of these input signals to generate feature vectors, or logical groupings of parameters associated with patients whose requests for dispensing prescribed medications have been associated with red flags, and/or evidence to support the validity of prescriptions or resolutions for those red flags. For example, the feature extraction functions 225 may generate a feature vector that indicates that for patients associated with a first set of two particular types of prescribed medications, the result is a red flag or a denial, while for patients associated with a second set of type types of prescribed medications, the result is that the prescribed medication is dispensed. As another example, the feature extraction functions 225 may generate a feature vector that indicates that for a patient prescribed a particular medication with an MME above a threshold value, the result is a red flag or denial, while for a patient prescribed the same medication with the same MME who is in hospice care, the result is no red flag (or the resolution of a red flag because of appropriate evidence to support the validity the prescription) and the prescribed medication is dispensed.

Accordingly, the feature extraction functions 225 can generate feature vectors 230 using the medication data 201, patient data 202, prescriber data 204, pharmacy data 206, and/or historical data 208. In general, the red flag identifier application 143 can train the red flag identifier machine learning model 144 using supervised learning, unsupervised learning, reinforcement learning, or any other suitable technique. Moreover, the red flag identifier application 143 can train the red flag identifier machine learning model 144 as a standard regression model.

Over time, as the red flag identifier application 143 trains the red flag identifier machine learning model 144, the red flag identifier machine learning model 144 can learn to predict whether a particular combination of medication data, patient data, prescriber data, and/or pharmacy data for a patient will result in a red flag or a denial, and/or whether there is sufficient evidence supporting the validity of the prescription for resolving any red flags. Additionally, the red flag identifier machine learning model 144 may learn to identify that a particular combination of medication data, patient data, prescriber data, and/or pharmacy data for a patient should result in a new type of red flag.

The red flag identifier machine learning model 144 may send indications of whether a medication prescribed to a current patient will result in a red flag and/or a denial, and/or whether there is evidence to support the validity of the prescription to resolve any red flags for the medication prescribed to the current patient, along with indications of any newly identified types of red flags, to the red flag identifier application 143, where they can be used, e.g., to determine whether dispensing the medication to the current patient would violate any regulations.

As new medication data 201, patient data 202, prescriber data 204, and pharmacy data 206 is collected, new training data can be generated and used in subsequent training of the red flag identifier machine learning model 144, i.e., for fine-tuning to improve the performance of the red flag identifier machine learning model 144.

Referring back to FIG. 1A, the back-end components 104 may include one or more administrator workstations 149. The administrator workstation 149 allows an authorized user to access the various applications running on the server 140 to alter or adjust the operation of the system 100. For example, a regulatory agency may change its rules regarding the use of patient medical records. The administrator may then access the server 140 via the administrator workstation 149 and alter rules active in the modules 142-144 to reflect the changes in regulatory or interested third party rules.

For purposes of implementing the system 100, the primary point of contact with the patient is through a pharmacy 110. The pharmacist filling the prescription will have access to one of the pharmacy workstations 128 and may invoke the system 100 when he or she fills the patient's prescription. Alternatively, the system 100 may be invoked automatically for each new prescription entered or by a broader system, such as a medication management system. In some embodiments, the system 100 may be accessed by one or more additional computing devices (not shown) via the network 130. In any case, the pharmacist may utilize a user interface 186 when dispensing (or attempting to dispense) prescriptions to patients.

Figure 3B:
Figure 3C:
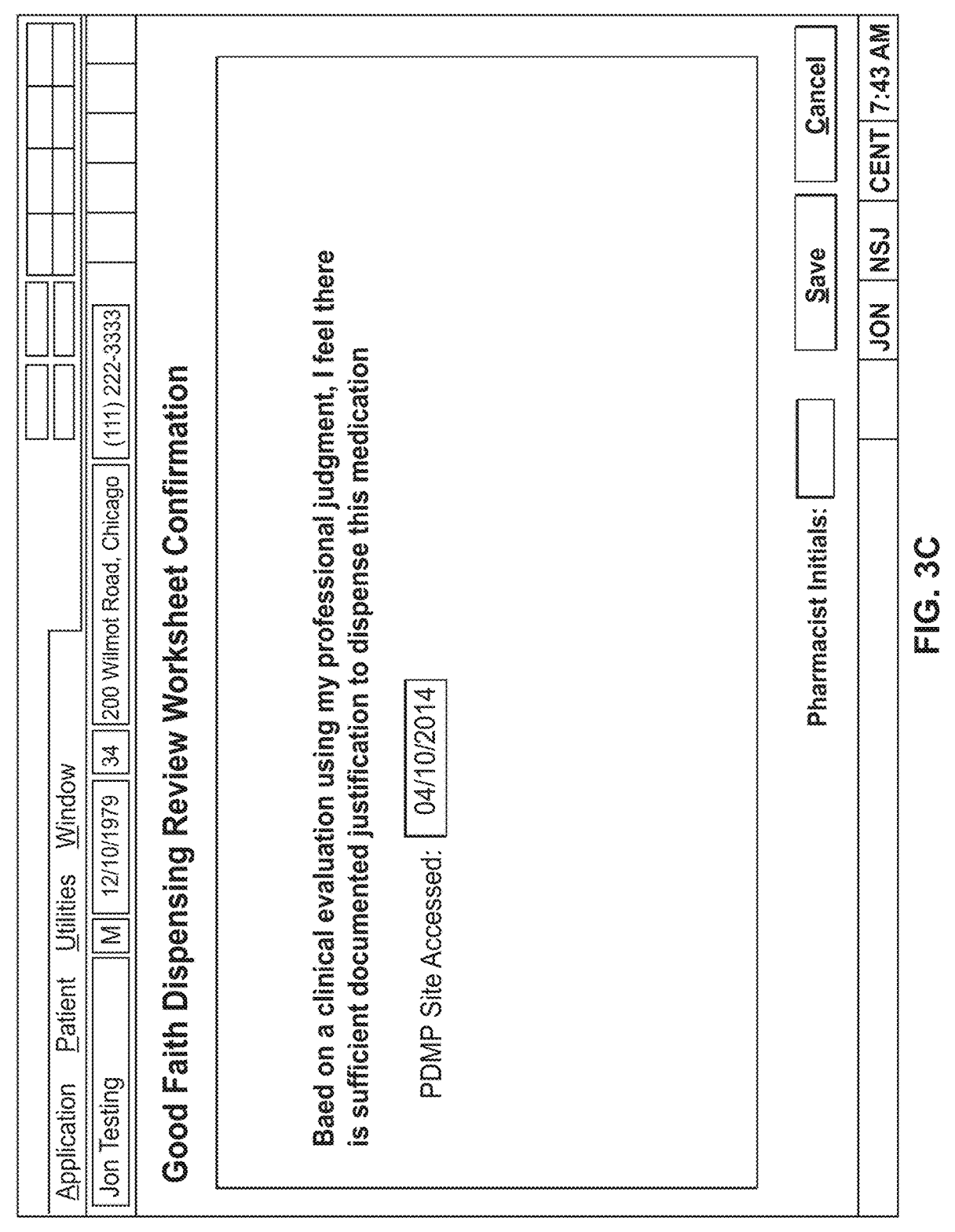

FIGS. 3A-3D illustrate example user interface display screens which may be used in the system of FIGS. 1A-1C for identifying red flags associated with dispensing a controlled substance to a particular patient, in accordance with some embodiments. For instance, the user interface display screens shown at FIGS. 3A-3D may be displayed by user interface displays 186 as shown in FIGS. 1A-1C. FIG. 3A illustrates an exemplary proprietary corresponding responsibility evaluation user interface screen that may be displayed as a pharmacist inputs patient information into the system. For instance, the pharmacist may capture an image of the patient's identification (e.g., a driver's license) and a prescription for the patient, and may input information obtained from patients that may be associated with red flags and/or evidence supporting the validity of a prescription and/or documented resolution for red flags via the user interface shown at FIG. 3A. FIG. 3B illustrates an exemplary patient information user interface screen that may be displayed as a patient requests or enters additional patient information. For instance, as shown in FIG. 3B, this additional patient information may include information associated with prescribers and dates and times of patient visits to each prescriber, as well as information associated with additional medications prescribed to the patient, and risks scores associated with medications prescribed to the patient. FIG. 3C illustrates an exemplary user interface screen that may be displayed to confirm that a pharmacist believes that evidence to support the validity of the prescriptions and/or documented resolutions s for any red flags associated with the patient are sufficient such that dispensing the medication to the patient will not violate regulations. Additionally, FIG. 3D illustrates an exemplary user interface screen prompting documentation of next steps taken by a pharmacist based on red flags, and in which the pharmacist may indicate which steps based on the red flags have been taken so far. The system of FIGS. 1A-1C may store inputs from the pharmacist via the user interface screens shown at FIGS. 3A-3D and may use this stored data in determining whether red flags should be generated for a particular patient, and, as discussed with respect to FIG. 2., this information may be used as historical training data when training a machine learning model to identify red flags.

Figure 4:
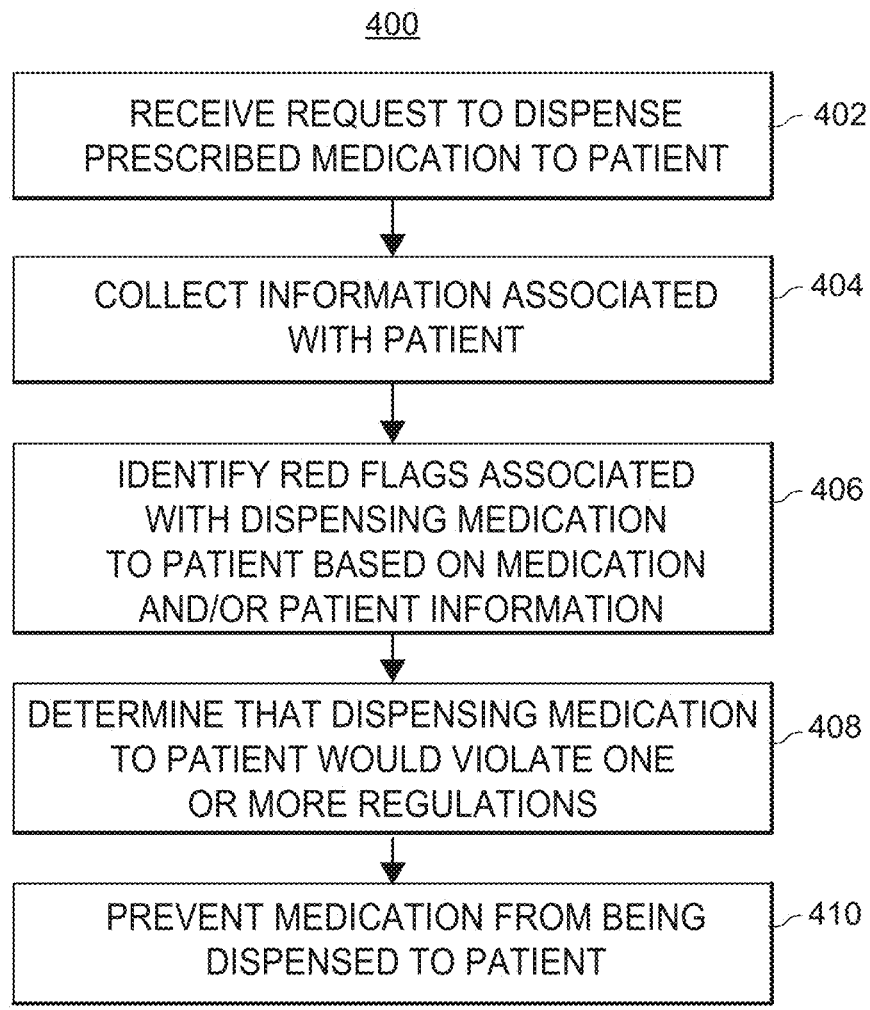
FIG. 4 illustrates a flow diagram of an exemplary method for identifying red flags associated with dispensing a controlled substance to a particular patient, in accordance with some embodiments.

Referring now to FIG. 4, a flow diagram of an exemplary computer-implemented method 400 for identifying red flags associated with dispensing a controlled substance to a particular patient is illustrated, in accordance with some embodiments. The method 400 can be implemented as a set of instructions (e.g., to be performed by the red flag identifier application 143) stored on a computer-readable memory and executable on one or more processors.

A request to dispense a medication prescribed to a patient may be received (block 402). For instance, a patient may enter a pharmacy to fill his or her prescription, or may order a prescription online or by mail.

Information associated with the patient may be collected (block 404) or otherwise obtained or accessed. Additionally, in some examples, information associated with the prescriber or pharmacy may be collected as well. In some examples, collecting the information may include receiving one or more inputs from a pharmacist associated with dispensing the medication to the patient, e.g., via a user interface. For instance, the pharmacist may input information provided by the patient, such as identification (or lack thereof) provided by the patient, address information provided by the patient, patient history information provided by the patient or known to the pharmacy, or other background information provided by the patient, e.g., based on questions asked by the pharmacist. Furthermore, the pharmacist may input information based on his or her observations of the patient, e.g., an observation that the patient appears sleepy or intoxicated, or otherwise appears to exhibit signs of an altered state. Moreover, in some examples, collecting the information may include obtaining information associated with the patient from other pharmacies within a network of pharmacies, or otherwise information associated with the patient stored on databases associated with the pharmacy or with the network of pharmacies, or databases created by governmental actors for the purposes of law enforcement (prescriptions drug monitoring programs (PDMP)).

Based on one or more of the prescribed medication, the information associated with the patient, and/or the information associated with the prescriber, one or more red flags associated with dispensing the prescribed medication to the patient may be identified (block 406) or generated. For instance, in some examples, red flags may be identified based at least partially on the type of medication prescribed (e.g., based on the medication being a controlled substance, based on the medication being an ingredient used to create a controlled substance, based on the medication being an immediate release medication, etc.). Additionally, in some examples, red flags may be identified based on the fact that the patient has been using a particular medication for a prolonged period of time. Moreover, in some examples, red flags may be identified based at least partially on the dosage of the medication or morphine milligram equivalent (MME), e.g., based on the dosage of the medication being greater than or equal to a threshold dosage amount, or based on the MME being greater than or equal to a threshold MME.

Furthermore, in some examples, red flags may be identified at least partially based on the prescribed medication as well as other medications prescribed to the patient or dispensed to the patient. For instance, the patient may be attempting to fill prescriptions for two different prescriptions simultaneously, or may have recently (e.g., within a threshold time period, such as several hours, or several days) filled a prescription for the other medication at an earlier time, and/or at a different pharmacy. The two medications may lead to a red flag, e.g., when one of the medications is an immediate release medication while the other medication is an extended release mediation, when the two medications may be combined to form a controlled substance, when both medications are controlled substances, when both medications are the same controlled substance, when both medications are otherwise the same medication, the same type of medication, or medications with similar or additive effects, etc. Moreover, in some examples, a red flag may be identified whenever a patient attempts to fill multiple prescriptions at multiple different pharmacies within a time period that is shorter than a threshold period of time (e.g., within several hours, within several days, etc.).

Additionally, in some examples, red flags may be identified at least partially based on previous instances in which prescribed medications for the patient were denied, rejected, or otherwise prevented from being dispensed to the patient. For instance, if a patient had previously attempted to fill a prescription for a controlled substance at the pharmacy, or at another pharmacy, and was denied based on red flags during the previous attempt, a red flag may be identified for any later attempts to fill prescriptions for controlled substances.

Moreover, in some examples, red flags may be identified at least partially based on the fact that the patient is attempting to refill a medication for the first time, or is attempting to refill the medication early.

Furthermore, in some examples, red flags may be identified at least partially based on the patient's method of payment. For instance, a red flag may be identified when a patient attempts to pay for a controlled substance prescription using cash or a discount card, as opposed to prescription insurance.

Additionally, in some examples, red flags may be identified at least partially based on a home address associated with the patient. For instance, a red flag may be identified based on the patient's home address, as provided by the patient, being invalid (e.g., on the fact that the address cannot be USPS standardized). As another example, a red flag may be identified based on a discrepancy between a home address associated with the patient and the address of the pharmacy or the address of the prescriber. For instance, a red flag may be identified when the distance between the patient's home address and the address of the pharmacy (or the distance between the patient's home address and an address associated with the prescriber) is greater than a threshold distance (e.g., 50 miles, 100 miles, 150 miles, etc.).

Moreover, in some examples, red flags may be generated at least partially based on the prescriber associated with the prescribed medication. For instance, a red flag may be identified when the prescriber is associated with previous instances in which the same patient or other patients have been denied their prescribed medications due to red flags or do not have individualized treatment plans. As another example, a red flag may be identified when the prescribed medication is outside of the scope of the prescriber's practice. For instance, a red flag may be identified if a prescribed medication unrelated to any skin conditions is prescribed by a prescriber who practices dermatology. Additionally, as another example, a red flag may be identified when the patient has been prescribed controlled substances by multiple different prescribers.

Furthermore, in some examples, red flags may be identified at least partially based on indications of the state of the patient observed by the pharmacist. For instance, if the patient appears sleepy, intoxicated, or otherwise appears to be in an altered state, a red flag may be identified for the patient.

In some examples, e.g., as discussed with respect to FIG. 2, the method 400 may further include training a machine learning model to identify new red flags associated with dispensing medications to patients using training data including: historical medications prescribed to historical patients, information associated with the historical patients, information associated with historical prescribers, information associated with historical pharmacies, and/or historical red flags associated with dispensing the historical medications to the historical patient identified by historical pharmacists. Accordingly, in such examples, identifying the red flags may include applying the machine learning model to the indication of the prescribed medication and/or the information associated with the patient.

Optionally, in some examples, the method 400 may further include analyzing the information associated with the patient to identify any evidence to support the validity of the prescription for each of the red flags associated with dispensing the medication to the patient. In some cases, red flags for which there is appropriate evidence to support the validity of the prescription may be resolved (block 408).

For instance, examples of evidence to support the validity of a prescription may include: the patient's identification being on file, no previous denials or refusals to dispense medications associated with the patient, the patient's insurance being a third party insurance provider, low MME associated with the prescribed medication, the patient being "opioid naïve," the duration of time for which the patient has taken the medication being low, an indication that the patient was previously prescribed naloxone, the patient being in hospice care (or being in institutional care,), certain patient diagnoses or health conditions (i.e., for which controlled substances are appropriate), and/or certain explanations by a patient. In some examples, evidence to support the validity of a prescription may generally serve to resolve red flags, while in other examples, certain evidence to support the validity of a prescription may be appropriate only for resolving particular red flags or particular types of red flags. For instance, the patient being in hospice care may be appropriate evidence supporting the validity of a prescription that serves to resolve many different types (or possibly all types) of red flags, because patients in hospice care may be appropriately prescribed frequent, high doses of controlled substances. In contrast, the patient's identification being on file may be evidence supporting the validity of a prescription that resolves only certain types of red flags, such as red flags associated with the patient's address. As another example, evidence supporting the validity of a prescription for a red flag associated with a discrepancy between the prescriber address or pharmacy address and the patient's home address may be that one or more of the prescriber address or pharmacy address are located nearby the patient's workplace.

In some examples, the method 400 may further include displaying (e.g., via a user interface) prompts for the pharmacist to follow up with the patient with additional questions, or otherwise obtain or collect additional information regarding the patient. For instance, additional questions may be used to confirm aspects of red flags, or aspects of evidence supporting the validity of a prescription. For example, if a red flag is generated because of a great distance between the patient's home address and the address of the pharmacy or the address of the prescriber, the pharmacist may be prompted to ask the patient if their workplace, school, daycare, or other frequently-visited location is near the pharmacy or the prescriber (possible evidence supporting the validity of a prescription when there is a great distance between the patient's home address and the address of the pharmacy or prescriber). If the patient responds that a frequently-visited location is near the pharmacy or prescriber, additional prompts may be displayed prompting the pharmacist to obtain proof or confirmation of one of these addresses (e.g., a workplace or school ID card, a pay stub including the workplace address, a bill including the daycare address, etc.). As another example, if a red flag is generated because of a high MME associated with the medication, a prompt may be displayed prompting the pharmacist to ask whether the patient is currently in hospice care (possible evidence supporting the validity of prescriptions for high MME medications), and if the patient responds that he or she is, the pharmacist may select an option indicating this answer, and an additional prompt may be displayed prompting the pharmacist to obtain proof or confirmation that the patient is in hospice care.

Additionally, in some examples, the method 400 may include training the same machine learning model discussed above (or a different machine learning model) to identify evidence supporting the validity of a prescription that is appropriate for various types of red flags using training data including: historical medications prescribed to historical patients, information associated with the historical patients, and/or historical red flags associated with dispensing the historical medications to the historical patient identified by historical pharmacists, as well as historical evidence supporting the validity of the prescription or resolution data for various red flags and indications of whether the red flags were resolved when the evidence supporting the validity of the prescription was provided. Accordingly, in such examples, determining whether evidence supporting the validity of a prescription is appropriate for a given set of red flags may include applying the machine learning model to the indication of the prescribed medication, the information associated with the patient, any identified red flags, and/or any provided evidence supporting the validity of the prescription.

In any case, based on the one or more identified red flags associated with dispensing the medication to the patient, a determination (block 310) may be made as to whether dispensing the medication to the patient would violate one or more regulations or not. These regulations may include Good Faith Dispensing regulations, other state or federal regulations associated with controlled substances, etc. For instance, if there are no red flags, or if all of the identified red flags associated with dispensing the medication to the patient have been resolved because there is appropriate evidence supporting the validity of the prescription for each red flag, dispensing the medication to the patient may not violate any regulations. In contrast, if there are remaining identified red flags associated with dispensing the medication for the patient, for which there is no appropriate evidence supporting the validity of the prescription, dispensing the medication to the patient may violate regulations.

Based on a determination that dispensing the medication to the patient would violate one or more regulations, the medication may be prevented (block 312) from being dispensed to the patient. For instance, preventing the medication from being dispensed to the patient may include displaying an indication, via a user interface, to a pharmacist indicating that the medication should not be dispensed. In some examples, the pharmacist may have the option to resolve the indication and dispense the medication based on his or her judgment. In some examples, preventing the medication from being dispensed to the patient may include displaying an indication, via a user interface, to a pharmacist indicating that the pharmacist should contact the prescriber of the medication to obtain additional information or evidence on whether the medication should be dispensed (e.g., to confirm that the correct medication was prescribed to the correct patient for the correct condition), prior to allowing the medication to be dispensed. Moreover, in some examples, preventing the medication from being dispensed to the patient may include automatically initiating communication (e.g., sending an email, text message, automated voice message, or other form of automatic communication) between the pharmacy and the prescriber to determine whether the medication should be dispensed (e.g., to confirm that the correct medication was prescribed to the correct patient for the correct condition), prior to allowing the medication to be dispensed. In some examples, preventing the medication from being dispensed to the patient may include causing, by a processor or controller, a case, shelf, or other storage unit storing the medication to be locked for use, e.g., for a certain period of time, such that the pharmacist is physically prevented from dispensing the medication to the patient during the period of time.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A computer-implemented method, comprising:
   training, by the one or more processors, using training data including at least one of: (i) historical medications prescribed to historical patients, (ii) information associated with the historical patients, and (iii) historical red flags associated with dispensing the historical medications to the historical patient identified by historical pharmacists, a machine learning model to identify red flags associated with dispensing medications to patients, wherein the training the machine learning model includes training the machine learning model using one of a supervised learning technique, an unsupervised learning technique, or a reinforcement learning technique;
   receiving, by one or more processors associated with a pharmacy, a request to dispense a medication prescribed to a patient;
   collecting, by the one or more processors, information associated with the patient, wherein the information associated with the patient includes two or more of: whether the patient provided identification at the pharmacy, conditions of the patient as observed by a pharmacist at the pharmacy, actions of the patient as observed by a pharmacist at the pharmacy, prescribers associated with the patient, a home address associated with the patient, dates of previous pharmacy visits by the patient, locations of previous pharmacy visits by the patient, payment methods used by the patient, previous instances in which prescribed medications for the patient were denied, rejected, or otherwise prevented from being dispensed, whether the patient is being treated by hospice or other institutionalized care, or an amount of time that the patient has been using a particular medication;
   identifying, by the one or more processors, by applying the trained machine learning model to one or more of the medication and the information associated with the patient, one or more red flags associated with dispensing the medication to the patient; determining, by the one or more processors, based on the one or more identified red flags associated with dispensing the medication to the patient, that dispensing the medication to the patient would violate one or more regulations; and
   preventing, by the one or more processors, the medication from being dispensed to the patient based on determining that dispensing the medication to the patient would violate one or more regulations,
   wherein preventing the medication from being dispensed to the patient includes causing, by the one or more processors, a storage unit for the medication to be locked for use for a certain period of time such that the pharmacist is physically prevented from dispensing the medication to the patient during the period of time.

2. The computer-implemented method of claim 1, further comprising, after preventing the medication from being dispensed to the patient, subsequently:
   analyzing, by the one or more processors, the information associated with the patient to identify evidence supporting the validity of a prescription for each of the one or more red flags associated with dispensing the medication to the patient; and
   resolving, by the one or more processors, the one or more red flags associated with dispensing the medication to the patient based on the identified evidence supporting the validity of the prescription for each of the one or more red flags.

3. The computer-implemented method of claim 1, wherein collecting information associated with the patient includes:
receiving, by a user interface, one or more inputs from a pharmacist associated with dispensing the medication to the patient.

4. The computer-implemented method of claim 1, wherein the one or more red flags associated with dispensing the medication to the patient are identified at least partially based on the type of medication prescribed to the patient.

5. The computer-implemented method of claim 1, wherein the one or more red flags associated with dispensing the medication to the patient are identified at least partially based on the dosage of the medication prescribed to the patient being greater than a threshold dosage amount.

6. The computer-implemented method of claim 1, wherein the medication prescribed to the patient is a first medication prescribed to the patient, and wherein the one or more red flags associated with dispensing the medication to the patient are identified at least partially based on the first medication and a subsequent medication(s) being prescribed to the patient.

7. The computer-implemented method of claim 1, wherein the one or more red flags associated with dispensing the medication to the patient are identified at least partially based on a previous instance in which a medication was prevented from being dispensed to the patient.

8. The computer-implemented method of claim 1, wherein the one or more red flags associated with dispensing the medication to the patient are identified at least partially based on an indication that a patient is attempting to refill the prescription for the medication prescribed to the patient for the first time.

9. The computer-implemented method of claim 1, wherein the one or more red flags associated with dispensing the medication to the patient are identified at least partially based on an indication that a patient is attempting to refill the prescription for the medication prescribed to the patient before a refill is required.

10. The computer-implemented method of claim 1, wherein the one or more red flags associated with dispensing the medication to the patient are identified at least partially based on an indication that the patient has recently attempted to fill prescriptions at a plurality of other pharmacies within a period of time that is less than a threshold period of time.

11. The computer-implemented method of claim 1, wherein the one or more red flags associated with dispensing the medication to the patient are identified at least partially based on a method of payment associated with the attempt to fill the prescription.

12. The computer-implemented method of claim 1, wherein the one or more red flags associated with dispensing the medication to the patient are identified at least partially based on a distance between a patient address associated with the patient and a pharmacy address associated with the pharmacy.

13. The computer-implemented method of claim 1, wherein the one or more red flags associated with dispensing the medication to the patient are identified at least partially based on an indication that a patient address associated with the patient is an invalid address.

14. The computer-implemented method of claim 1, further comprising:

collecting, by the one or more processors, information associated with a prescriber of the medication; and
wherein the one or more red flags associated with dispensing the medication to the patient are identified at least partially based on one or more previous medications prescribed by the prescriber having been prevented from being dispensed to respective patients.

15. The computer-implemented method of claim 1, further comprising
collecting, by the one or more processors, information associated with a prescriber of the medication; and
wherein the one or more red flags associated with dispensing the medication to the patient are identified at least partially based on the prescribed medication being outside of a scope of a practice of the prescriber.

16. The computer-implemented method of claim 1, further comprising
collecting, by the one or more processors, information associated with the prescriber of the medication; and
wherein the one or more red flags associated with dispensing the medication to the patient are identified at least partially based on a distance between a prescriber address associated with the prescriber and a patient address associated with the patient or a distance between the prescriber address and a pharmacy address associated with the pharmacy.

17. The computer-implemented method of claim 1, further comprising:
receiving, by a user interface, one or more inputs from a pharmacist associated with dispensing the medication to the patient; and
wherein the one or more red flags associated with dispensing the medication to the patient are identified at least partially based on the one or more inputs indicating that the pharmacist observed one or more signs of intoxication associated with the patient.

18. A computer system, the computer system comprising:
one or more processors; and
a non-transitory program memory communicatively coupled to the one or more processors and storing executable instructions that, when executed by the one or more processors, cause the computer system to:
train, using training data including at least one of: (i) historical medications prescribed to historical patients, (ii) information associated with the historical patients, and (iii) historical red flags associated with dispensing the historical medications to the historical patient identified by historical pharmacists, a machine learning model to identify red flags associated with dispensing medications to patients, wherein the training the machine learning model includes training the machine learning model using one of a supervised learning technique, an unsupervised learning technique, or a reinforcement learning technique;
receive a request to dispense a medication prescribed to a patient;
collect information associated with the patient, where in the information associated with the patient includes two or more of: whether the patient provided identification at the pharmacy, conditions of the patient as observed by a pharmacist at the pharmacy, actions of the patient as observed by a pharmacist at the pharmacy, prescribers associated with the patient, a home address associated with the patient, dates of previous pharmacy visits by the patient, locations of previous pharmacy visits by the patient, payment methods used by the patient, previous instances in which prescribed medications for the patient were denied, rejected, or otherwise prevented from being dispensed, whether the patient is being treated by hospice or other institutionalized care, or an amount of time that the patient has been using a particular medication;

identify, based on one or more of the medication and the information associated with the patient, one or more red flags associated with dispensing the medication to the patient;

determine, by applying the trained machine learning model to the one or more identified red flags associated with dispensing the medication to the patient, that dispensing the medication to the patient would violate one or more regulations; and prevent the medication from being dispensed to the patient based on determining that dispensing the medication to the patient would violate one or more regulations, wherein preventing the medication from being dispensed to the patient includes causing, by the one or more processors, a storage unit for the medication to be locked for use for a certain period of time such that the pharmacist is physically prevented from dispensing the medication to the patient during the period of time.

19. A tangible, non-transitory computer-readable medium storing executable instructions that, when executed by at least one processor of a computer system, cause the computer system to:

train, using training data including at least one of: (i) historical medications prescribed to historical patients, (ii) information associated with the historical patients, and (iii) historical red flags associated with dispensing the historical medications to the historical patient identified by historical pharmacists, a machine learning model to identify red flags associated with dispensing medications to patients, wherein the training the machine learning model includes training the machine learning model using one of a supervised learning technique, an unsupervised learning technique, or a reinforcement learning technique;

receive a request to dispense a medication prescribed to a patient;

collect information associated with the patient, wherein the information associated with the patient includes two or more of: whether the patient provided identification at the pharmacy, conditions of the patient as observed by a pharmacist at the pharmacy, actions of the patient as observed by a pharmacist at the pharmacy, prescribers associated with the patient, a home address associated with the patient, dates of previous pharmacy visits by the patient, locations of previous pharmacy visits by the patient, payment methods used by the patient, previous instances in which prescribed medications for the patient were denied, rejected, or otherwise prevented from being dispensed, whether the patient is being treated by hospice or other institutionalized care, or an amount of time that the patient has been using a particular medication;

identify, by applying the trained machine learning model to one or more of the medication and the information associated with the patient, one or more red flags associated with dispensing the medication to the patient;

determine, based on the one or more identified red flags associated with dispensing the medication to the patient, that dispensing the medication to the patient would violate one or more regulations; and prevent the medication from being dispensed to the patient based on determining that dispensing the medication to the patient would violate one or more regulations, wherein preventing the medication from being dispensed to the patient includes causing, by the one or more processors, a storage unit for the medication to be locked for use for a certain period of time such that the pharmacist is physically prevented from dispensing the medication to the patient during the period of time.

* * * * *